United States Patent [19]
Fitzhugh et al.

[11] Patent Number: 5,698,693
[45] Date of Patent: Dec. 16, 1997

[54] PROCESS OF SEPARATING THE DIASTEREOMERS OF (6R,6S) -5,6,7,8-TETRAHYDROFOLIC ACID DERIVATIVES

[75] Inventors: Anthony L. Fitzhugh; Rhone K. Akee, both of Frederick, Md.

[73] Assignee: The United States of America as represented by the Department of Health and Human Services, Washington, D.C.

[21] Appl. No.: 977,008

[22] Filed: Nov. 16, 1992

[51] Int. Cl.[6] .................................................. C07D 475/04
[52] U.S. Cl. .................................................. 544/258
[58] Field of Search ................................. 544/258, 251

[56] References Cited

U.S. PATENT DOCUMENTS

| | | | |
|---|---|---|---|
| 4,959,472 | 9/1990 | Wood et al. | 544/158 |
| 5,006,655 | 4/1991 | Müller et al. | 544/158 |
| 5,010,194 | 4/1991 | Müller et al. | 544/158 |
| 5,153,309 | 10/1992 | Fitzhugh | 530/333 |
| 5,194,611 | 3/1993 | Marazza et al. | 544/158 |
| 5,239,074 | 8/1993 | Marazza et al. | 544/251 |

FOREIGN PATENT DOCUMENTS 8808844   11/1988   WIPO .

OTHER PUBLICATIONS

Fitzhugh et al, Scalable Route to Resolving Monoesters of dl 5–Formyl 5,6,7,8–Tetrahydropteroylmono–L–Glutamic Acid, Pteridines vol. 3, pp. 99–100.

Choi et al, Resolution of the Stereoisomers of Leucovorin and Methyltetrahydrofolate by Chiral High–Performance Liquid Chromatography, (1988), Analytical Biochemistry 168, pp. 398–404.

Rees et al, Asymmetric Reduction of Dihydrofolate Using Dihydrofolate Reductase and Chiral Boron–Containing Compounds, Tetrahedron, vol. 42, No. 1, pp. 117–136, (1986).

Cosulich et al J. Am. Chem. Soc., (1952) 74, 4215, Diastereoisomers of Leucovorin.

Kaufman et al, Chromatrographic Separaton of the Diastereoisomers of dl, L–5,10–Methylenetetrahydrofolate, The Journal of Biological Chemistry, (1963) vol. 238, No. 4, pp. 1498–1500.

Hillcoat et al, The Reduction of Folate by Borohydride and by Dithionite, Biochemical and Biophysical Research Communications, (1964), vol. 15 No. 4 pp. 303–307.

Matthews et al, Inhibition of Pig Liver Methylenetetrahydrofolate Reductase by Dihydrofolate: Some Mechanistic and Regulatory Implications, (1979) Biochemistry, vol. 18, No. 22, pp. 4845–4851.

Feeney et al, Hydrogen–1 Nuclear Magnetic Resonance Study of the Complexes fo Two Distereoisomers of Folinic Acid with Dihydrofolate Reductase, (1981) Biochemistry, vol. 20, pp. 1837–1842.

Wainer et al, Direct resolution of the stereoisomers of leucovorin and 5–methyltetrahydrofolate using a bovine serum albumin high–performance liquid chromatographic chiral stationary phase coupled to an achiral phenyl column, (1988) Journal of Chromatography, vol. 424, pp. 158–162.

Fitzhugh et al, A New and Facile Synthetic Route to $N^5$–Formyl Tetrahydropteroylpoly–L–Glutamates[1], (1991), Bioorganic & Medicinal Chemistry Letters, vol. 1, No. 3, pp. 155–158.

Fitzhugh and Akee, Chem. Abstr. vol 117 Entry 251731t (1992).

Fitzhugh and Chmurny and Klose Chem. Abst. vol. 115 Entry 159734g (1991).

*Primary Examiner*—Donald G. Daus
*Attorney, Agent, or Firm*—Spencer & Frank

[57] ABSTRACT

A method for resolving 5,6,7,8-tetrahydrofolic acid derivatives into diastereomerically pure 6R and 6S forms. The method comprises (1) alpha esterification of the tetrahydrofolic acid derivative; (2) resolution of the alpha monoester into pure diastereomer; and (3) deprotecting the resolved alpha monoester to thereby produce the pure diastereomer of the original 5,6,7,8 tetrahydrofolic acid derivative. The resolution step can be carried out by any conventional means including chromatography or fractional crystallization. The method results in absolute diastereomeric purity even when an achiral stationary phase is used for the resolution.

9 Claims, No Drawings

PROCESS OF SEPARATING THE DIASTEREOMERS OF (6R,6S) -5,6,7,8-TETRAHYDROFOLIC ACID DERIVATIVES

FIELD OF INVENTION

The present invention relates to a method of resolving mixtures of (6R, 6S)-5,6,7,8-tetrahydrofolic acid derivatives into their pure (6R) and (6S) forms.

BACKGROUND

Folic acid (I) and its derivatives have become important substances in combatting such diseases as cancer, opportunistic infections, autoimmune diseases, and megaloblastic anemia, and as assays in developing new antifolates. In nature these compounds function as coenzymes in one-carbon unit transfer reactions that lead to the biosynthesis of certain nucleic and amino acids. Folic acid itself is a naturally occurring compound and is an N-substituted derivative of L-glutamic acid bearing the chemical designation N-(Pteroyl)-L-glutamic acid. Functionally, the molecule's structure may be divided into three regions: (i) a pteridine ring, (ii) a p-aminobenzoyl ring, and (iii) an L-glutamic acid moiety, also known as an α-S-glutamic acid moiety.

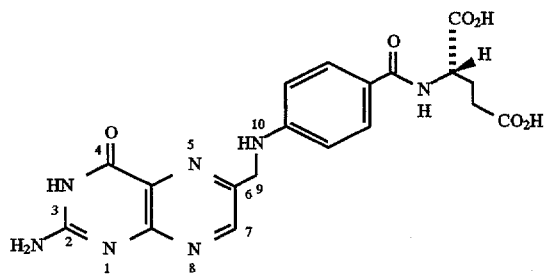

In vivo the pteridine ring of folic acid is reduced to tetrahydrofolic acid in a two-step process by reaction with nicotinamide dinucleotide phosphate, reduced form (NADPH) and dihydrofolate reductase (EC 1.5.1.3, DHFR). The first step results in the formation of 7,8-dihydrofolic acid (II) while the second step yields 5,6,7,8-tetrahydrofolic acid (III). The second step also generates a new chiral center at carbon atom 6, which is designated (6S) in the Cahn-Ingold-Prelog system.

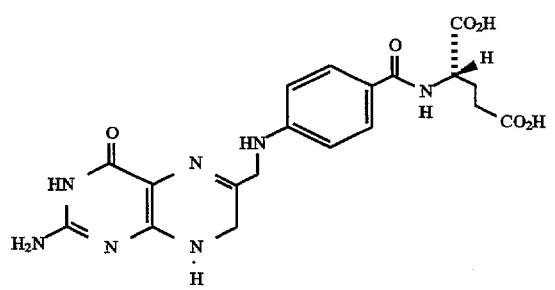

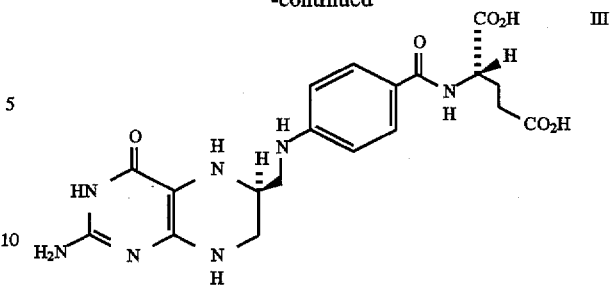

The nitrogen atoms at positions 5 and 10 of the tetrahydrofolic acid (III) undergo subsequent substitution reactions to give a number of derivatives (IVa–f).

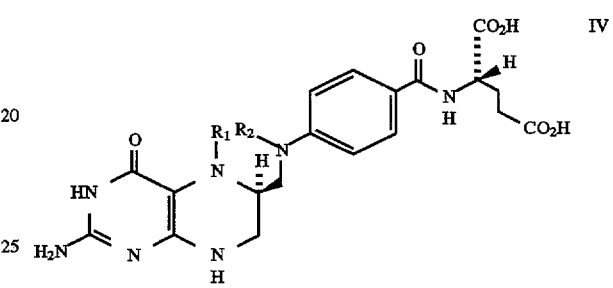

IVa $R_1 =$ —CHO, $R_2 =$ H
b $R_1 =$ —CNH, $R_2 =$ H
c $R_1 =$ —CH$_3$, $R_2 =$ H
d $R_1 =$ H, $R_2 =$ —CHO
e $R_1 + R_2 =$ —CH$_2$—
f $R_1 + R_2 =$ —CH—

It should be noted that while the 5-substituted derivatives of (6S)-5,6,7,8-tetrahydrofolic acid are designated as (6S), the 10-substituted and 5+10 substituted derivatives of (6S)-5,6,7,8-tetrahydrofolic acid are designated as (6R), even through the orientation of the chiral 6 carbon atom is not changed. Further, most 5 and 5+10 substituted derivatives of (6S)-5,6,7,8-tetrahydrofolic acid exist in a trans configuration relative to substituents on nitrogen atom 5 and carbon atom 6 [Poe, M., Benkovic, S. J., *Biochemistry*, 19, 4576–4582 (1980); Fontecilla-Camps, J. C., et al., *J. Am. Chem. Soc.*, 101, 6114–6115 (1979)]. The stereochemistry is important since only the naturally occurring form, as shown above, will be taken up into the cells. Thus, when used as an antifolate rescue agent, i.e., providing the naturally occurring derivatives whose formation has been prevented by the administration of an antifolate, only the naturally occurring stereochemical form is effective.

Synthetic means for producing III, and hence the naturally occurring form of the subsequent derivatives, is known through the combination of enzymatic and/or chemical means. A classic route to III comprises: (i) the chemical reduction of folic acid (I) with Zn or Na$_2$S$_2$O$_4$ to form 7,8-dihydrofolic acid (II); (ii) enzymatic reduction with DHFR and NADPH to produce (6S)-5,6,7,8-tetrahydrofolic acid (III); and then (iii) chemical derivatization to give IVa–f. While this route is widely used in the folate field, it has inherent weaknesses that restrict its scalability and hence is unsuitable for producing large quantities or commercial application [Rees, L., et al., *Tetrahedron*, 42, 117–136 (1986)].

Alternatively, the production of 5,6,7,8-tetrahydrofolic acid derivatives by a wholly chemical route produces (6R, 6S) mixtures. The 5-substituted and 5+10-substituted (6R, 6S)-5,6,7,8-tetrahydrofolic acid derivatives are diastereomeric since there are two stereocenters (the 5-nitrogen and 6-carbon atoms), whereas the unsubstituted and the 10-substituted (6R,6S)-5,6,7,8-tetrahydrofolic acid derivatives are enantiomeric, having only one stereocenter (the 6-carbon atom). Although separation of the enantiomers is apparently unknown in the prior art, resolution of the diastereomers has been attempted with some success. [See Kaufman et al., *J. Biol. Chem.*, 238, 1498–1500 (1963); Hillcoat, B. L., Blakley, R. L., *Biochem. Biophys. Res. Commun.*, 15, 303–307 (1964); Matthews, R. G., Haywood, B. J., *Biochemistry*, 18, 4845–4851 (1979); Feeney, J., et al., *Biochemistry*, 20, 1837–1842 (1981); Wainer, I. W., Stiffin, R. M., *J. of Chromatography*, 424, 158–162 (1988), which are all incorporated by reference and which detail the direct resolution of (6R,6S) mixtures of 5 and 5+10-substituted derivatives (IVa, c and e).]

In general, these wholly chemical routes to producing IVa, c and e (the natural forms) proceed in a three-step manner. In the first step, folic acid is reduced with either $PtO_2$ or Pd-C to yield a ~50:50 mixture of (6R) and (6S)-5,6,7,8-tetrahydrofolic acid. In the second and third steps, the mixture is derivatized to a diastereomeric mixture of 5-formyl, 5-methyl, or 5,10-methylene 5,6,7,8-tetrahydrofolate and chromatographed on a chiral stationary phase (e.g., triethylaminoethyl (TEAE), diethylamnoethyl (DEAE)-cellulose, and albumin-linked silica gel [Kaufman, Hillcoat, Matthews, Feeney, Wainer, supra]. Unfortunately, the diastereomers are poorly resolved by most of these methods and all suffer from the fact that they are only suitable for the isolation of milligram or smaller amounts.

Chiral column chromatography has recently been replaced by a fractional crystallization method developed by Mueller and coworkers [Mueller, H. R., et al., *Int. Pat. PCT Int. Appl.* WO 88/08,844 (Cl. C07D475/04), 15 May 1987, and its equivalent, U.S. Pat. No. 5,134,235 which is incorporated by reference]. Their method teaches that IVa preferentially precipitates from a diastereomeric mixture of 5-formyl 5,6,7,8-tetrahydrofolate in a saturated aqueous solution of calcium chloride. Repeated recrystallization results in diastereomeric purity approaching 98 to 99%. Mueller's method has the additional benefit of being easily scaled to multigram levels. While the diastereomeric purity of IVa obtained by this method is suitable in most uses (e.g., as an antifolate rescue agent), it is unacceptable in experiments involving the kinetic analysis of folate-dependent enzymes. Studies of this type require material of absolute (100%) chiral purity. Indeed, the presence of even minute (0.1 to 1%) quantities of an unnatural diastereomer (particularly if it acts as an inhibitor), may lead to the compilation of erroneous data [Smith, G. K., et al., *Biochemistry*, 20, 4034–4039 (1981)].

Thus, in the prior art there is no method which can achieve both large quantities of product and have absolute diastereometric purity.

SUMMARY OF THE INVENTION

It is an object of the present invention to provide a method for resolving mixtures of (6R,6S)-diastereomers of 5,6,7,8-tetrahydrofolic acid derivatives into their pure (6R) and (6S) forms.

It is another object of the present invention to provide a scalable method for resolving mixtures of (6R,6S)-diastereomers of 5,6,7,8-tetrahydrofolic acid derivatives into their pure (6R) and (6S) forms in large quantities.

It is another object of the present invention to provide a method for resolving mixtures of (6R,6S)-diastereomers of 5,6,7,8-tetrahydrofolic acid derivatives through the use of a simple achiral chromatographic procedure.

These and other objects of the present invention have been accomplished by a method for resolving a mixture of (6R,6S)-diastereomers of 5,6,7,8-tetrahydrofolic acid derivative which comprises:

(a) α-esterifying a (6R,6S)-5,6,7,8-tetrahydrofolic acid derivative according to formula VIII:

wherein $R_1$ is $C_1$–$C_6$ alkyl, $C_1$–$C_6$ alkyl carbonyl, $C_1$–$C_6$ alkoxy carbonyl, or —CHO, wherein said alkyl, alkyl carbonyl, and alkoxy carbonyl may be substituted with halogen, $C_1$–$C_6$ alkoxy, or phenyl; $R_2$ is H, $C_1$–$C_6$ alkyl, $C_1$–$C_6$ alkyl carbonyl, $C_1$–$C_6$ alkoxy carbonyl, or —CHO, wherein said alkyl, alkyl carbonyl, and alkoxy carbonyl may be substituted with halogen, $C_1$–$C_6$ alkoxy, or phenyl; or $R_1$ and $R_2$ join together to form a one carbon bridge between the 5 and 10 positions; so as to produce a (6R,6S) monoester according to formula IX:

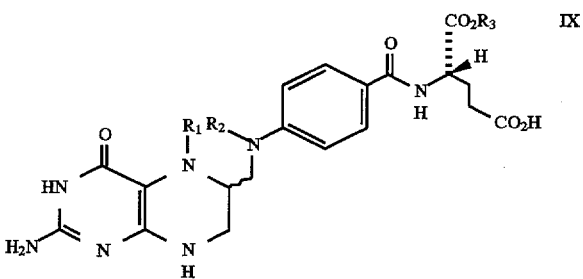

wherein $R_1$ and $R_2$ are as defined in formula VIII and $R_3$ is a protecting group;

(b) separating the (6S) and (6R) form of said α-monoester by chromatography or fractional crystallization; and (c) deprotecting said separated (6S) or (6R) α-monoester, thereby producing pure (6S)- or (6R)-5,6,7,8-tetrahydrofolic acid derivative.

Applicants have discovered that the α-monoester represented by formula IX will readily separate into its diastereomerically pure (6R) and (6S) forms. Even more surprising, Applicants have discovered that absolute diastereomeric purity can be obtained chromatographically by using an achiral stationary phase. Hence the use of the more complex and expensive chiral stationary phase used in the prior art can be avoided by the present invention.

DETAILED DESCRIPTION OF THE INVENTION

Preferably, the compounds that are separated by the present invention have the formula VIa and VIb.

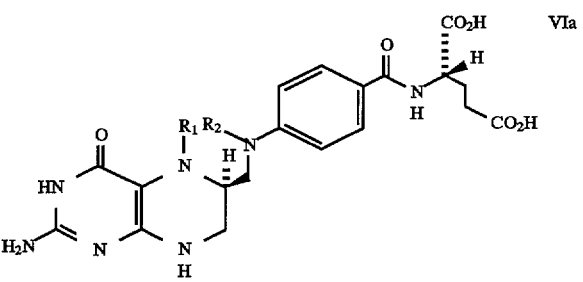

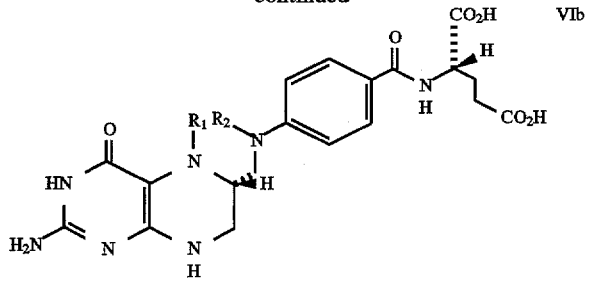

Wherein $R_1$ is $C_1$–$C_6$ alkyl, $C_1$–$C_6$ alkyl carbonyl, $C_1$–$C_6$ alkoxy carbonyl, or —CHO, each of which (except —CHO) may be substituted by halogen, $C_1$–$C_6$ alkoxy or phenyl; e.g., acetyl, t-butyl, 2,2-dichloroacetyl, benzoyl, t-butoxy carbonyl, benzyloxy carbonyl; $R_2$ is H, $C_1$–$C_6$ alkyl, $C_1$–$C_6$ alkyl carbonyl, $C_1$–$C_6$ alkoxy carbonyl, or —CHO, each of which (except —CHO) may be substituted by halogen, $C_1$–$C_6$ alkoxy or phenyl; e.g., acetyl, t-butyl, 2,2-dichloroacetyl, benzoyl, t-butoxy carbonyl, benzyloxy carbonyl; or $R_1$ and $R_2$ together form a one carbon bridge between positions 5 and 10. VIa and VIb exist in nature. Alternatively, they can be prepared synthetically by conventional techniques.

Several reports guided the development of this invention: (i) the observation that in the presence of one equivalent of base, the α-carboxyl group of an N-substituted L-glutamic acid derivative ionizes approximately 70 to 100 times more than the γ-carboxyl group; hence, reaction with an alkyl or aryl halide should result in the preferential formation of an α-monoester of 5-formyl 5,6,7,8-tetrahydrofolic acid [Nefkens, G. H. L., *Peptides,* Proc. European Symp. 5th, 1962 (Pub. 1963), 39–40, Oxford; Nefkens, G. H. L., Nivard., R. J. F., *Rec. Trav. Chem.,* 83, 199–207 (1964), which are both incorporated by reference]; (ii) the ease with which α,γ-diesters of folinic acid are formed with alkyl or aryl halides and excess base in dimethylsulfoxide [Rosowsky, A., Yu, C.-S., "*Chem. Biol. Pteridine*": Dev. Biochem., 4, 6th, Kisliuk, R. K., Brown, G. M. (Eds.), pp. 273–277, 1978 (Pub. 1979), Elsevier/North-Holland: New York, which is hereby incorporated by reference in its entirety]; (iii) the observations that (6R,6S) diastereomeric mixtures of 5-formyl, 5-methyl, and, 5,10-methylene-5,6,7,8-tetrahydrofolic acid are separable on chiral stationary phases such as TEAE/DEAE-cellulose or albumin-linked silica gel [Kaufman, Hillcoat, Matthews and feeney, supra]; and, (iv) the nuclear magnetic resonance (NMR) and x-ray crystallographic evidence that reduced folate derivatives bearing a substituent on the 5 nitrogen atom are always oriented in as trans configuration with respect to the p-aminobenzoyl-L-glutamic acid group at the 6 carbon atom [Poe and Fontecilla-Camps, supra].

A chemically derived mixture of VIa and VIb is converted to its (6R,6S)-α-monoester form (VII) to (i) enhance its solubility in organic solvents and (ii) maximize its capacity for sorbents such as silica gel.

Wherein $R_1$ and $R_2$ are as defined for (VIa and b), wherein $R_3$ is independently $C_1$–$C_8$ alkyl, $C_5$–$C_6$ cycloalkyl, substituted $C_5$–$C_6$ cycloalkyl, $C_6$–$C_{10}$ aryl (phenyl and naphthyl), substituted $C_6$–$C_{10}$ aryl, $C_6$–$C_{10}$ aryl $C_1$–$C_8$ alkyl, substituted $C_6$–$C_{10}$ aryl $C_1$–$C_8$ alkyl, diphenylmethyl, substituted diphenyl methyl and trialkylsilyl. The substituents can be any organic or inorganic moiety that does not adversely affect the $R_3$ group's ability to function as an easily removable protecting group. Preferably $R_3$ is $C_1$–$C_6$ alkyl, substituted $C_1$–$C_6$ alkyl, $C_5$–$C_6$ cycloalkyl, phenyl, substituted phenyl, benzyl, substituted benzyl, diphenylmethyl and triethylsilyl.

Most preferably $R_3$ is methyl, ethyl, propyl, butyl, sec-butyl, t-butyl, pentyl, hexyl, cyclopentyl, cyclohexyl, methoxymethol, ethoxymethyl, methylthiomethyl, 2,2,2-trichloroethyl, 2-bromoethyl, phenyl, benzyl, 2-chlorobenzyl, 2,6-dichlorobenzyl, diphenylmethyl and triethylsilyl. Examples of the substituents which can number up to three, are methyl, ethyl, $C_1$–$C_3$ alkoxy, $C_1$–$C_3$ thiol and halogen. By halogen is meant fluorine, chlorine, bromine and iodine, preferably chlorine and bromine. By alkyl is meant a straight chain saturated hydrocarbon moiety.

The invention provides a process for the preparation of pure (6R) and (6S)-5,6,7,8-tetrahydrofolic acid derivatives. In a preferred embodiment the invention comprises the steps of: (1) preferential attachment of a protecting group such as an alkyl, aryl, or trialkylsilyl substituent to the α-carboxyl group of a (6R,6S) α-monoester of 5,6,7,8-tetrahydrofolic acid derivative; (2) optionally, isolation of the crude (6R,6S) α-monoester of 5,6,7,8-tetrahydrofolic acid derivative from contamination with α-γ-diester, γ-monoester or diacid derivatives; (3) chromatographic separation of the (6R,6S) α-monoester mixture into pure (6R) and (6S)-5,6,7,8-tetrahydrofolic acid derivatives on an achiral stationary phase; (4) removal of the protecting group to give the desired 5,6,7,8-tetrahydrofolic acid derivatives as diacids or salts thereof. In another embodiment fractional crystallization is used instead of chromatography in order to resolve the diastereomers.

The advantage of this process over prior art is that it is scalable and yields (6R) and (6S) diastereomers of 5 6 7 8-tetrahydrofolic acid derivatives having absolute (100%) diastereomeric purity. The prior art methods result in the formation of 5,6,7,8-tetrahydrofolic acid derivatives that are either (i) of absolutely (100%) diastereomeric purity but produced in small amounts (typically, 5 mg or fewer) or (ii) of less than absolute diastereomeric purity (~98–99%) but produced in large (multigram) amounts. At this stage, the use of enzymes and cofactors make the former method expensive, while the lack of absolute diastereomeric purity makes the latter method's use in kinetic assays precarious.

The steps in the resolution are written out below in more detail and in structural terms:

STEP 1

Synthesis of the α-Monoesterified Intermediate

A compound of formula VIII wherein $R_1$ and $R_2$ are as above, is subjected to an esterification reaction which converts it to IX.

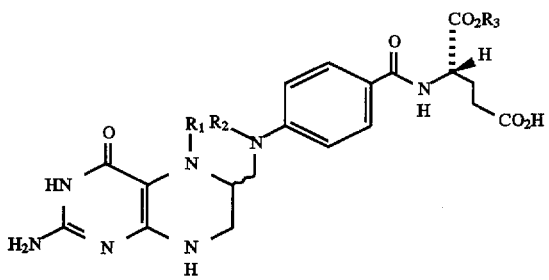

The reaction is carried out by any means known to the art (see, for example, Nefkens et al., *Rec. Tray. Chem.*, 83, 199–207 (1964), which is incorporated by reference). Most preferably by reacting a compound of the formula $R_3$—X, wherein $R_3$ is the same compound of formula VIII. The reaction is carried out in the presence of base in a polar aprotic solvent. Suitable bases are carbonates, bicarbonate, hydroxides, hydrides, amides and amines (both aliphatic and aromatic). The base should be strong enough to remove the α-carboxyl hydrogen quantitatively. Examples of suitable bases include $NaHCO_3$, $NA_2CO_3$, $Na_2CO_3$, $NAH_2$, $NANH_2$, $KHCO_3$, $K_2CO_3$, $LiHCO_3$, $Li_2CO_3$, NAOH, KOH, LiOH, triethylamine, diisopropylethylamine, 4-methylmorpholine, 2,6-di-t-butylpyridine, tetrabutylmmonium hydroxide and the like. The molar ratio of base to the compound of formula VIII should be 1.5 to 0.5, preferably about 1.0. Suitable organic solvents include DMF (dimethylformamide), DMA (dimetholacdetamide), DMSO (dimethylsulfoxide) and HMPT (hexamethylphosphoramide). The molar ratio of $R_3$—X to compound VIII is in the range of 1.5 to 05 and preferably is about 1. The temperature range for the reaction with $R_3$—X is –50° C. to +150° C. , preferably about +25° C. The reaction is carried out at atmospheric pressure under an inert atmosphere of dry nitrogen or argon. Esterification results in mostly the desired (6R,6S) α-monoesterified product. Impurities such as the α,γ-diester or γ-monoester may be removed, thereby isolating the α-monoester, by any suitable and conventional technique for purification such as high pressure liquid chromatography, column chromatography or fractional crystallization. It should be noted, however, as is well understood in the art, that such a purification step, even one using high pressure liquid chromatography, does not result in the resolution of the diastereomers because of the different parameters employed during purification and resolution. For instance, for chromatographic purification purposes, it is conventional in the art to use a stationary phase having a particle size of about 0.035–0.075 mm, while the particle size for the stationary phase used in resolution is generally about 0.003–0.016 mm. Similarly, the use of different solvents can cause the fractional crystallization technique to serve as either a purification means or a resolution means. Thus, this optional purification step refers to those conventional techniques and their corresponding appropriate parameters well known in the art that result in the isolation of the α-monoester.

Suitable (6R,6S) reduced folate derivatives for the preparation of their α-monoesters in STEP 1 include: 5,6,7,8-tetrahydrofolic acid, 5-methyl 5,6,7,8-tetrahydrofolic acid, 5,10-methylene 5,6,7,8-tetrahydrofolic acid, 5,10-methenyl 5,6,7,8-tetrahydrofolic acid (with a suitable counter ion selected from chloride, bromide, iodide, fluoride, formate, trifluoroacetate, acetate, sulfate, phosphate and the like), 5-formyl 5,6,7,8-tetrahydrofolic acid, 5,10-diformyl 5,6,7,8-tetrahydrofolic acid, 5-t-butoxy carbonyl 5,6,7,8-tetrahydrofolic acid and 5,10-di-5-butoxy carbonyl 5,6,7,8-tetrahydrofolic acid, 5-carbobenzyloxy 5,6,7,8-tetrahydrofolic acid, 5,10-discarbobenzyloxy 5,6,7,8-tetrahydrofolic acid. 5-formyl 5,6,7,8-tetrahydrofolic acid, however, is the preferred derivative for the purpose of this invention. Most of the starting compounds are commercially available, also, see *Methods of Enzymology*, Vol. 6, pp. 802–815 (1963); Temple., C., Jr., Montgomery, J. A., *"Folates and Pterins"*, Vol. 1, Blakley, R. L., and Benkovic, S. J. (Eds.), Wiley: New York, pp. 62–120 (1984), which are incorporated by reference. These references teach how to make several of the reduced folate compounds.

The (6R,6S)-α-monoester derivatives (IX) are disclosed in U.S. Pat. No. 5,153,309 to Fitzhugh, which is incorporated by reference.

STEP 2

Separation of the (6R,6S) Diastereomers of Formula IX

The (6R,6S) diastereomeric mixtures of formula (IX) are separated into their pure natural (Xa) and nonnatural configurations (Xb)

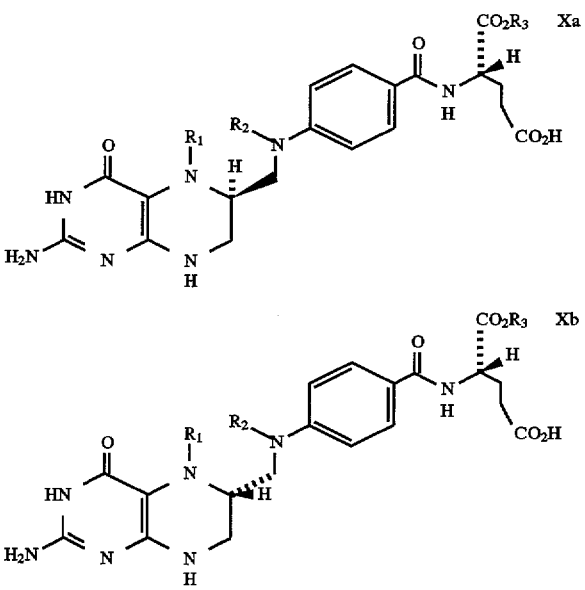

wherein $R_1$, $R_2$ and $R_3$ are the same as above. The separation of the (6R,6S) diastereomers of (IX) can be carried out by any of the known methods in the art for the resolution of diastereomers, such as, high pressure liquid chromatography, column chromatography or fractional crystallization. Most preferably, however, the separation is carried out using an achiral stationary phase and achiral solvents on a high pressure liquid chromatography column. The achiral stationary phases can be silica gel, alumina, graphic carbon, magnesium silicate, controlled-pure glass, hydroxylapatite, octadecyl silica gel, octyl silica gel, hexyl silica gel, dimethyl silica gel, trimethyl silica gel, cyclohexyl silica gel, phenyl silica gel, diphenyl silica gel, dimethylamino silica gel and the like. Most preferably, however, is silica gel. The temperature range for the separation is from about -20° C. to +150° C., preferably about +25° C. Suitable solvents for the separation include water, acetic acid, formic acid, trifluoroacetic acid, triethylamine, methanol, ethanol, 1-propanol, 2-propanol, t-butanol, methylene chloride, 1,2-dichloromethane, chloroform, tetgrahydroforan, p-dioxane and the like. Most preferably, however, are mixtures of the aforementioned compounds.

STEP 3

Deprotection of Compounds of Formula (Xa and b)

The compounds of formula (Xa or b) are treated with a reagent which removes the $R_1$, $R_2$ and $R_3$ groups together or independently. Suitable reagents are well known in the art of peptide synthesis [Greene, Th. W., *"Protective Groups in Organic Synthesis"*, Wiley: New York, pp. 152–187 (1981), which pages are incorporated by reference]. Inorganic/organic bases, acids or reducing agents are suitable. Examples of the bases include aqueous alkaline earth metal or alkali metal hydroxides, or tertiary or quaternary C1–$C_4$ alkyl ammonium hydroxides; specifically magnesium, calcium, sodium and potassium hydroxides and trimethyl, triethyl, tetramethyl or tetraethyl, ammonium hydroxides. Also, $NaSCH_3$, $NaSCH_3CH_3$, $NaO_2$, $Ba(OH)_2$, KSCN, $Na_2CO_3$, $NaHCO_3$, $K_2CO_3$, $KHCO_3$, $Li_2CO_3$, $LiHCO_3$, $KSeO_3K$ and the like. Examples of the acids include trifluoroacetic acid, formic acid, acetic acid, gaseous hydrogen chloride and hydrogen bromide, and optionally in water or a water miscible solvent such as methanol, ethanol, 1-propanol, 2-propanol, acetonitrile, tetrahydrofuran, p-dioxane, dimethylformamide and the like. Examples of the reducing agents include $PtO_2$, Pt on activated carbon, Pt on alumina, Pt black, Pt, Pd (II) acetate, Pd hydroxide on carbon, Pd on activated carbon, Pd on alumina, Pd on barium carbonate, Pd on barium sulfate, Pd on calcium carbonate, Pd on calcium carbonate, poisoned with lead, Pd(II) oxide, Pd (II) trifluoroacetate, $Na_2S$, $Na_2S_2O_4$, $ZnCl_2$, Zn, and the like. Other suitable methods include enzymatic cleavage. Examples of enzymatic cleavage reaction include cholesterol esterase, porcine liver esterase, protease, porcine pancreatic lipase, α-chymotrypsin, chymotrypsin, bakers yeast and the like (see Larock, R. C., *"Comprehensive Organic Transformations"*, VCH, New York (1989), pp. 981–985, which pages are incorporated by reference).

The following example serves only to illustrate the present invention and should not be considered as limiting the scope thereof.

EXAMPLES

Example 1

Preparation of the α-2,6-Di-Chlorobenzyl Monoester of (6R,6S) -5-Formyl 5,6,7,8-Tetrahydrofolic Acid 500 mg of (6R,6S) 5-formyl 5,6,7,8-tetrahydrofolic acid and 56 mg of $Na_2CO_3$ were added to 20 mL of dimethylsulfoxide 317 mg of α-2,6-dichlorobenzyl bromide was added and the mixture stirred at room temperature for 15 hours. The reaction mixture was then poured into 250 mL of ice-cold water and the copious yellow-orange precipitate collected by centrifugation. The precipitate was suspended in an additional 250 mL of ice-cold water and centrifuged a second time. The filtrate was discarded and the precipitate freeze-dried over a 48-hour period. The dry, crude mixture was next purified by flash chromatography [Still et a, *J. Org. Chem*, 43, 2923–2925 (1970)]over silica gel (mixture of particle sizes ranging from 0.03 –0.075 mm; 10:1 (v/v) $CHCl_3$—MeOH]. The product containing fractions (50 mL) were combined and dried in vacuo to give 293 mg of the pure α-2,6-dichlorobenzyl monoester of 5-formyl 5,6,7,8-tetrahydrofolic acid: mp >300 C; IR (KBr) wavenumber 3345, 1730, 1620, 1325, 1188, 770; 1H 500 MHz NMR ($Me_2SO$-$d_6$) delta, in ppm relative to TMS 1.97 (cm,2H), 2.21(cm,2H), 2.80(cm,1H), 3.07(cm,1H), 3.13(dd, J=4.1, 12.6 Hz,1H), 3.41(dd,J=5.1,12.7,1H), 4.32(cm, 1H), 4.78 (cm,1H), 5.26, 5.32(AB, J=12 Hz,2H), 6.31(x of ABX, 1H), 6.57(BB' of AA' BB',2h), 6.69(bs,1H), 6.97(x of ABX,1H), 7.44(B of $A_2B$,1H), 7.53 ($A_2$ of $A_2B$,2H), 7.60 (vb,1H), 7.64 (AA' of AA' BB',2H), 8.825, 8.832 (3.3 Hz, aldehyde rotomers,1H), 9.13(bs,1H), 11.3 (bs,1H); MSHRFAB) m/z found 632.1480 (M+), calcd. for $C_{27}H_{27}Cl_2N_7O_7$) 632.1424.

Example 2

Separation of the α-2,6-Dichlorobenzyl Monoester of (6R, 6S)-5-Formyl 5,6,7,8-Tetrahydrofolic Acid 20 mg of α-2,6-dichlorobenzyl monoester of (6R,6S)-5-formyl 5,6,7,8-tetrahydrofolic acid (dissolved in 500 mL of 5:1 $CHCl_3$—MeOH) injected onto a 41.4 mm ×25 cm silica gel column (average particle size about 0.008 mm; 90:10:03 (v/v) $CHCl_3$—MeOH-acetic acid) at a flow rate of 81 mL/min with 254 nm detection. The two peaks that emerged were collected in separate flasks designated A and B. This process was repeated 10 additional times (200 mg total). Excess solvent was evaporated and the resulting solids dried in vacuo to give 81 mg of peak A and 86 mg of peak B, respectively.

The resulting solids were subjected to IR, MSHRFAB, and 1H NMR analyses and gave satisfactory results. The identity of the natural diastereomer was tentatively established through chromatographic comparison on a 4.6mm ×25 cm silica gel column (90:10:0.03 (v/v) $CHCl_3$—MeOH-acetic acid) at a flow rate of 1 ml/min with 254 nm detection. The authentic α-2,6-dichlorobenzyl monoester of (6S)-5-formyl 5,6,7,8-tetrahydrofolic acid eluted in a manner identical to peak B.

Example 3

Deprotection of the Pure (6R) and (6S) Diastereomers of 5-Formyl -5,6,7,8-Tetrahydrofolic Acid 1 mg of solid from peaks A and B was added to two 12 mL test tubes containing 10 mL of 0.1N NaOH. After 10 minutes, the pH of the solution was adjusted to 7 with acetic acid in an ice-water bath. Injection of these solutions onto an albumin column [after the method of Wainer, I. W., Stiffen, R. M., *J. Chromatography*, 424, 158–162 (1988)]provided unequivocal evidence that peak A was the pure (6R)-diastereomer, while peak B was the pure (6S)-diastereomer.

What is claimed is:

1. A method for resolving a mixture of (6R,6S)-diastereomers of 5,6,7,8-tetrahydrofolic acid derivative which comprises:

(a) α-esterifying a (6R,6S)-5,6,7,8-tetrahydrofolic acid derivative according to formula VIII:

wherein R1 is $C_1$–$C_6$ alkyl, $C_1$–$C_6$ alkyl carbonyl, $C_1$–$C_6$ alkoxy carbonyl, or —CHO, wherein said alkyl, alkyl carbonyl, and alkoxy carbonyl may be substituted with halogen, $C_1$–$C_6$ alkoxy, or phenyl; $R_2$ is H, $C_1$–$C_6$ alkyl, $C_1$–$C_6$ alkyl carbonyl, $C_1$–$C_6$ alkoxy carbonyl, or —CHO, wherein said alkyl, alkyl carbonyl, and alkoxy carbonyl may be substituted with halogen, $C_1$–$C_6$ alkoxy, or phenyl; or $R_1$ and $R_2$ join together to form a one carbon bridge between the 5 and 10 positions; so as to produce a (6R,6S) monoester according to formula IX:

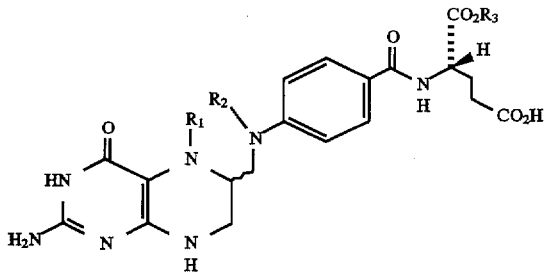

wherein $R_1$ and $R_2$ are as defined in formula VIII and $R_3$ is a protecting group;

(b) separating the (6S) and (6R) form of said α-monoester by chromatography or fractional crystallization; and (c) deprotecting said separated (6S) or (6R) α-monester, thereby producing pure (6S)- or (6R)-5,6,7,8-tetrahydrofolic acid derivative.

2. The method according to claim 1, wherein said separation step (b) is carried out using high pressure liquid chromatography or column chromatography.

3. The method according to claim 2, wherein said separation is carried out using an achiral stationary phase.

4. The method according to claim 3, wherein said separation is carried out using a high pressure liquid chromatography column having an achiral stationary phase and achiral solvents.

5. The method according to claim 1, wherein said α-esterification step (a) comprises reacting said derivative of formula VIII with a compound of the formula $R_3$–X, wherein $R_3$ is as defined in formula IX and X is a halogen.

6. The method according to claim 5, wherein $R_3$ is $C_{1-C8}$ alkyl, $C_5$–$C_6$ cycloalkyl, substituted $C_5$–$C_6$ cycloalkyl, $C_6$–$C_{10}$ aryl (phenyl and naphthyl), substituted $C_6$–$C_{10}$ aryl, $C_6$–$C_{10}$ aryl $C_1$–$C_8$ alkyl, substituted $C_6$–$C_{10}$ aryl $C_1$–$C_8$ alkyl, diphenylmethyl, substituted diphenyl methyl and trialkylsilyl.

7. The method according to claim 5, wherein said α-esterification step (a) is carried out in the presence of a base in a polar aprotic solvent.

8. The method according to claim 1, wherein said α-esterification step (a) further comprises purifying the crude α-monoester product so as to remove any produced α,γ-diester or γ-monoester.

9. A method for separating α-monoesters of a (6R,6S) mixture of 5,6,7,8-tetrahydrofolic acid derivatives, which comprises:

subjecting a mixture of (6R,6S)-5,6,7,8-tetrahydrofolate represented by formula IX to high pressure liquid chromatography, column chromatography or fractional crystallization, thereby separating said mixture into 100% diastereomerically pure (6R)- and 100% diastereomerically pure (6S)-5,6,7,8-tetrahydrofolate:

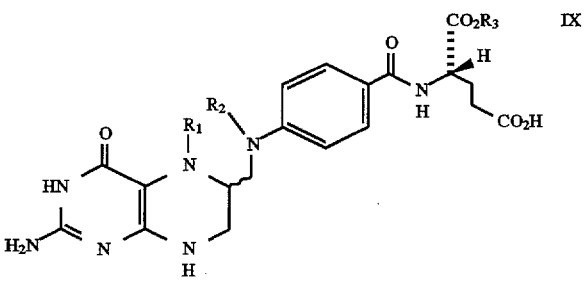

wherein $R_1$ is $C_1$–$C_6$ alkyl, $C_1$–$C_6$ alkyl carbonyl, $C_1$–$C_6$ alkoxy carbonyl, or —CHO, wherein said alkyl, alkyl carbonyl, and alkoxy carbonyl may be substituted with halogen, $C_1$–$C_6$ alkoxy, or phenyl; $R_2$ is H, $C_1$–$C_6$ alkyl, $C_1$–$C_6$ alkyl carbonyl, $C_1$–$C_6$ alkoxy carbonyl, or —CHO, wherein said alkyl, alkyl carbonyl, and alkoxy carbonyl may be substituted with halogen, $C_1$–$C_6$ alkoxy, or phenyl; or $R_1$ and $R_2$ join together to form a one carbon bridge between the 5 and 10 positions; and $R_3$ is $C_1$–$C_8$ alkyl, $C_5$–$C_6$ cycloalkyl, substituted $C_5$–$C_6$ cycloalkyl, $C_6$–$C_{10}$ aryl (phenyl and naphthyl), substituted $C_6$–$C_{10}$ aryl, $C_6$–$C_{10}$ aryl $C_1$–$C_8$ alkyl, substituted $C_6$–$C_{10}$ aryl $C_1$–$C_8$ alkyl, diphenylmethyl, substituted diphenyl methyl and trialkylsilyl.

* * * * *